(12) United States Patent
Pierce et al.

(10) Patent No.: US 8,998,824 B2
(45) Date of Patent: Apr. 7, 2015

(54) BIOLOGICAL SAMPLE COLLECTION DEVICE

(75) Inventors: Alan Stuart Pierce, Cardiff (GB); Cheryl Louise Potts, Cardiff (GB); Simon Laurence John Stubbs, Cardiff (GB); David Gwyn Treharne, Newport (GB)

(73) Assignee: GE Healthcare UK Limited, Little Chalfont (GB)

( * ) Notice: Subject to any disclaimer, the term of this patent is extended or adjusted under 35 U.S.C. 154(b) by 0 days.

(21) Appl. No.: 14/122,291

(22) PCT Filed: May 24, 2012

(86) PCT No.: PCT/EP2012/059683
§ 371 (c)(1),
(2), (4) Date: Nov. 26, 2013

(87) PCT Pub. No.: WO2012/163788
PCT Pub. Date: Dec. 6, 2012

(65) Prior Publication Data
US 2014/0100480 A1    Apr. 10, 2014

(30) Foreign Application Priority Data

May 27, 2011 (GB) .................... 1108962.0

(51) Int. Cl.
*A61B 5/00* (2006.01)
*A61B 10/00* (2006.01)
(52) U.S. Cl.
CPC ......... *A61B 10/0051* (2013.01); *A61B 10/0045* (2013.01); *A61B 10/0096* (2013.01)

(58) Field of Classification Search
USPC ......... 600/572, 573; 73/864.91; 422/406, 409
See application file for complete search history.

(56) References Cited

U.S. PATENT DOCUMENTS

| 2,905,169 | A | * | 9/1959 | Nieburgs | 600/572 |
| 5,308,580 | A | | 5/1994 | Clark | |
| 6,464,939 | B1 | * | 10/2002 | Bachand et al. | 422/411 |
| 7,294,502 | B2 | | 11/2007 | Eckermann et al. | |
| 7,458,941 | B2 | * | 12/2008 | Caillouette | 600/572 |
| 7,993,283 | B1 | * | 8/2011 | Altschul | 600/573 |
| 2004/0171173 | A1 | | 9/2004 | Eckermann et al. | |

(Continued)

FOREIGN PATENT DOCUMENTS

WO    WO 2007/099344    9/2007
WO    WO 2008/099196    8/2008

*Primary Examiner* — Max Hindenburg
(74) *Attorney, Agent, or Firm* — Sutherland Asbill & Brennan LLP

(57) ABSTRACT

Biological samples, such as saliva, are commonly collected on a swab and subsequently transferred to an absorbent storage medium. Embodiments of the present invention provide a biological sample collection device comprising a collection portion and a body portion, the body portion including a holding portion for holding a biological sample storage medium, and a sample transfer means, such as a cover. The collection portion can be arranged in a first position separated from the body portion for collecting a sample, and in a second position at least partly between the sample transfer means and the holding portion, with the sample transfer means being operable to push the collection portion towards a position at which the holding means is arranged to hold the biological sample storage medium, enabling a sample held in the collection portion to be transferred to the latter. This provides an improved means of collecting a biological sample.

18 Claims, 9 Drawing Sheets

(56) References Cited

U.S. PATENT DOCUMENTS

2009/0208371 A1    8/2009    Hannant et al.
2010/0101340 A1    4/2010    Lipscombe
2010/0106057 A1    4/2010    Harvey et al.

\* cited by examiner

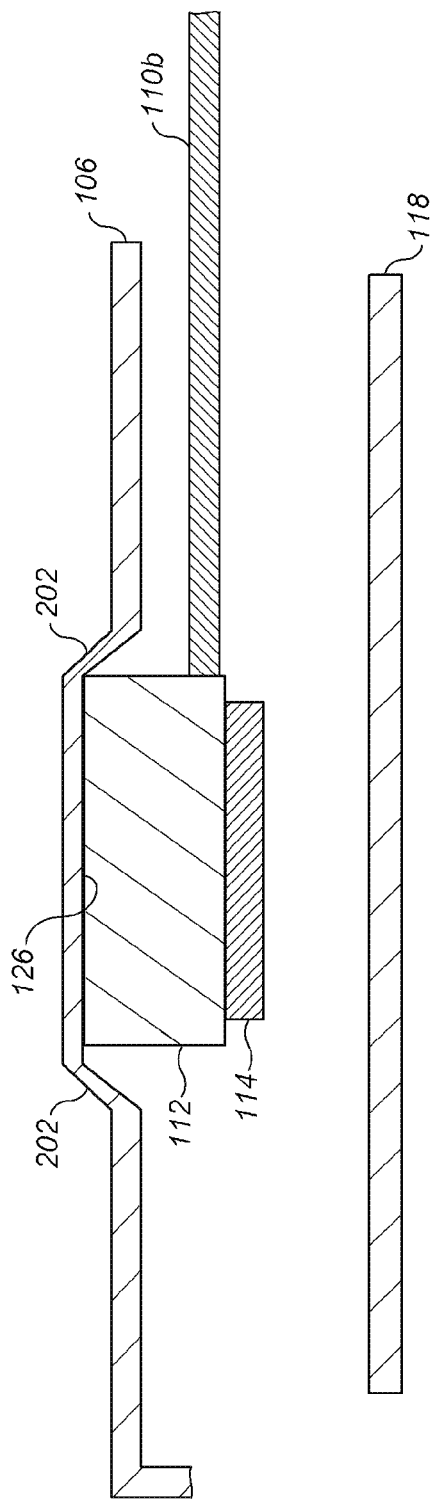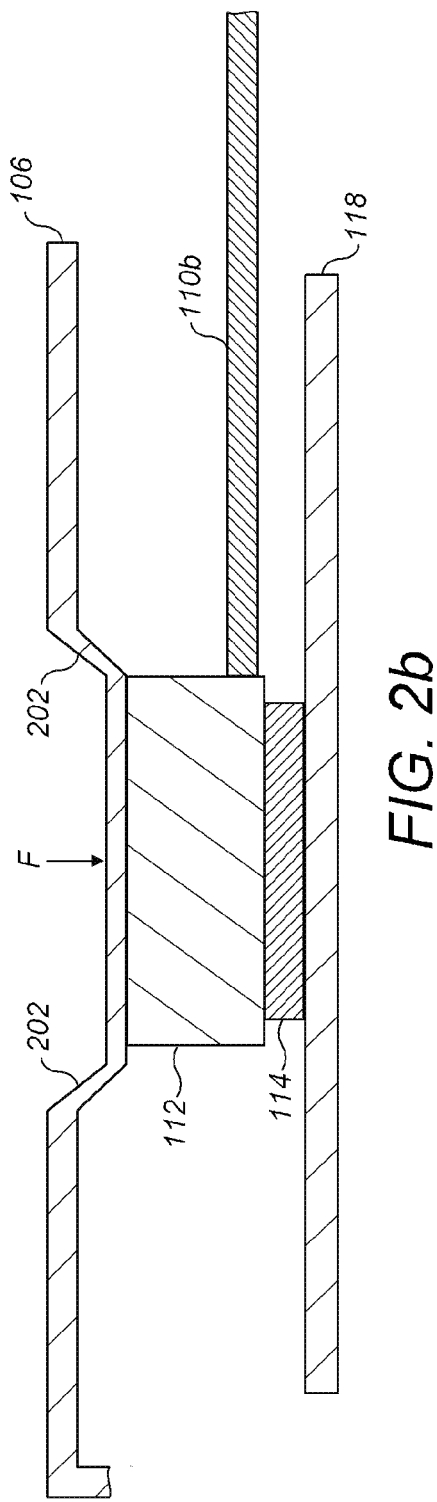

BIOLOGICAL SAMPLE COLLECTION DEVICE

CROSS-REFERENCE TO RELATED APPLICATIONS

This application is a filing under 35 U.S.C. 371 of international application number PCT/EP2012/059683, filed May 24, 2012, published on Dec. 6, 2012 as WO 2012/163788, which claims priority to application number 1108962.0 filed in Great Britain on May 27, 2011.

FIELD OF THE INVENTION

The present invention relates to a device for collecting and storing biological samples.

BACKGROUND OF THE INVENTION

Biological samples, such as saliva taken for DNA profiling in criminal investigations, are commonly taken by swabbing a liquid containing biological material with an absorbent collection medium. Such collection media are, by necessity, exposed, and are therefore vulnerable to contamination. To maintain the integrity of the samples, they are typically transferred to and held in an absorbent storage medium, which may comprise a membrane impregnated with chemicals for stabilising the sample. The samples are allowed to dry and, once dry, the biological storage medium can be stored or transported to a testing facility for analysis.

Such methods of transferring biological samples from the collection medium to the storage medium typically involve bringing the collection medium into physical contact with the storage medium, perhaps with the application of a moderate amount of mechanical force; some of the liquid sample is then drawn by capillary action into the sample storage medium. Conventionally, this is a manual process and therefore consistent and uniform transfer of the biological sample from the collection medium to the storage medium depends heavily on the skill of the operator.

US2008/196517 proposes an integrated collection, transfer, and storage device into which a biological sample storage medium may be inserted. The device comprises a sample collection surface that can be brought into physical contact with the sample storage medium. However, the construction of the device is such that direct contact between the operator and the collection portion of the device is necessary to transfer biological material; this is undesirable, as it may result in contamination of the sample and/or discomfort for the operator. Further, the force applied by an operator to cause transfer of the biological material may be uneven, causing the resulting transfer to be inconsistent and non-uniform.

It is an object of the present invention to mitigate the problems of the prior art.

SUMMARY OF THE INVENTION

In accordance with an aspect of the present invention, there is provided a biological sample collection device, comprising:

a collection portion carrying a biological sample collection medium; and a body portion comprising a storage medium holding portion for holding a biological sample storage medium at a holding position, and a sample transfer means, the collection portion being movably connected to the body portion, whereby the biological sample collection device is capable of being configured according to a first configuration and according to a second, different, configuration, wherein:

in said first configuration, the collection portion is at a first position spatially separated from the body portion for collecting a biological sample on the biological sample collection medium; and in said second configuration, the collection portion is at a second position at least partly between the sample storage medium holding portion and the sample transfer means, and the sample transfer means is operable to apply a force to the collection portion, whereby said collection portion is compelled towards said holding position so that, when the storage medium holding portion holds a biological sample storage medium, the biological sample collection medium is pushed against said biological sample storage medium.

By providing a sample transfer means which is operable to apply a force to the collection portion to transfer a biological sample from the collection medium to the storage medium, the sample can be transferred from the sample collection medium to the sample storage medium, without any direct contact between the operator and the sample collection portion. Further, the more evenly applied pressure allowed by indirectly transmitting the force and spreading the load over a larger area results in a uniform transfer of the sample from the collection portion to the storage medium holding portion.

Preferably, when the collection portion is at said second position, the biological sample collection medium is in a position separated from said holding position. This facilitates faster post-collection drying of the sample.

In some embodiments, the collection portion is connected to the body portion via an arm portion that is arranged to flex from said second position towards the holding position in response to said force.

In some embodiments, the sample transfer means comprises a substantially flat cover portion. This enables the biological sample collection device to be substantially flat, which is convenient for subsequent storage and transportation of the device. The biological sample collection device may be arranged such that, when the collection portion is at said second position, the collection portion is at least partly enclosed by the cover portion and the storage medium holding portion. This provides protection to the biological sample after transfer to the biological sample storage medium.

In some embodiments, the sample transfer means comprises a compressible recess portion, and said operation of the sample transfer means comprises compression of the recess portion. The recess portion may have at least one dimension substantially matching a corresponding dimension of the collection portion, so that the collection portion may locate in said recess portion when the device is in the second configuration. The recess portion may thus serve as guide the collection portion so that the latter is correctly located with respect to the biological sample storage medium, improving the reliability of sample transfer thereto.

In some embodiments, the collection portion is connected to the storage medium holding portion via a swivel joint, which enables the collection portion to move between said first position and said second position. The storage medium holding portion may define a plane for holding said biological sample storage medium and the swivel joint may enable the collection portion to swivel about an axis substantially within said plane.

In some embodiments, the swivel joint enables the collection portion to swivel about an axis substantially perpendicular to said plane. A gap may be provided between the sample transfer means and the storage medium holding portion and the swivel joint may enable the collection portion to move through said gap. This enables the sample transfer means to be fixed with respect with to the storage medium holding portion, allowing a simple structure for the biological sample collection device.

In some embodiments, the collection portion is connected to the storage medium holding portion via a slide joint, which enables translation of the collection portion between said first position and said second position.

In some embodiments, the sample transfer means is movably connected to said storage medium portion between an open position, for facilitating movement of the collection portion from said first position to said second position, and a closed position for enabling operation of the sample transfer means to apply said force.

In some embodiments, a locking means is provided for locking said sample transfer means in at least one of said closed position and said open position. This reduces the risk of the sample being exposed to contamination.

In some embodiments, a locking means is provided for locking said collection portion in at least one of said first position and said second position.

In some embodiments, the sample collection medium comprises an absorbent material for absorbing a liquid biological sample.

In some embodiments, the storage medium holding portion holds a biological sample storage medium.

In some embodiments, the biological sample storage medium is removable from said storage medium holding portion.

In some embodiments, the biological sample storage medium comprises a planar membrane for absorbing liquid biological samples.

In some embodiments, the biological sample storage medium is held on a card.

In some embodiments, the biological sample collection device is made from a plastics material.

Further features and advantages of the invention will become apparent from the following description of illustrative embodiments of the invention, given by way of example only, which is made with reference to the accompanying drawings.

BRIEF DESCRIPTION OF THE DRAWINGS

FIG. 1c shows a side view of the biological sample collection device of FIG. 1a;

FIG. 2a shows a partial section view of a sample transfer means of the biological sample collection device of FIG. 1 in a first position;

FIG. 2b shows the sample transfer means of FIG. 2a in a second position;

DETAILED DESCRIPTION OF THE INVENTION

Figure 1A:
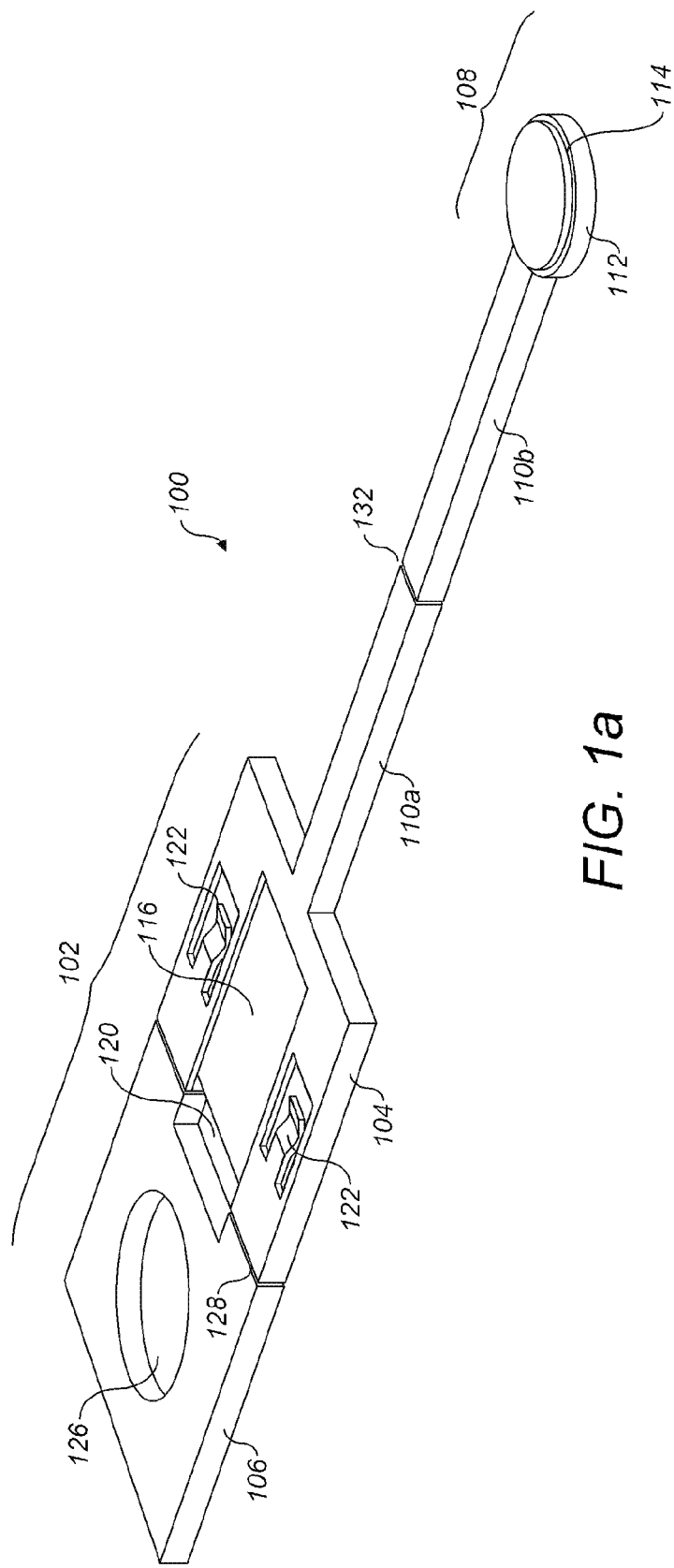
FIG. 1a shows a perspective view of a biological sample collection device in a first configuration according to a first embodiment of the present invention.
Figure 1B:
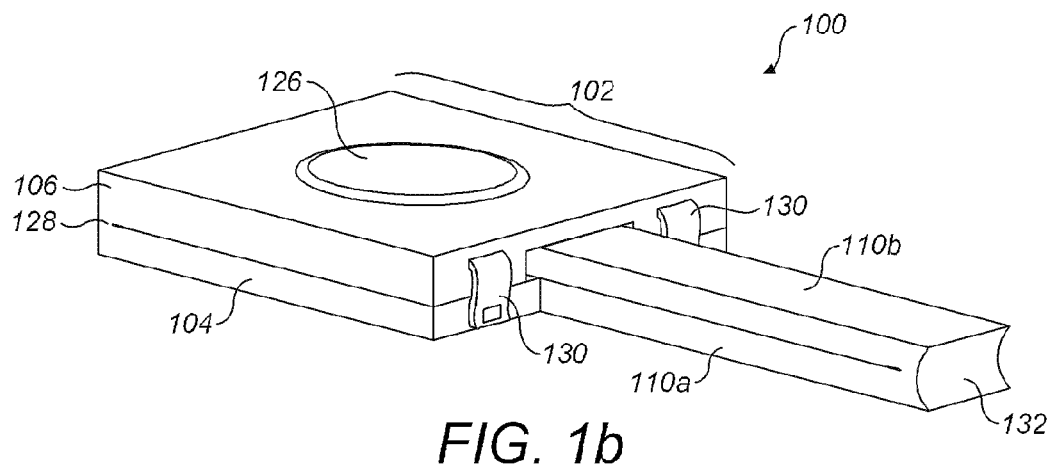
FIG. 1b shows a perspective view of the biological sample collection device of FIG. 1a in a second configuration.
Figure 1C:
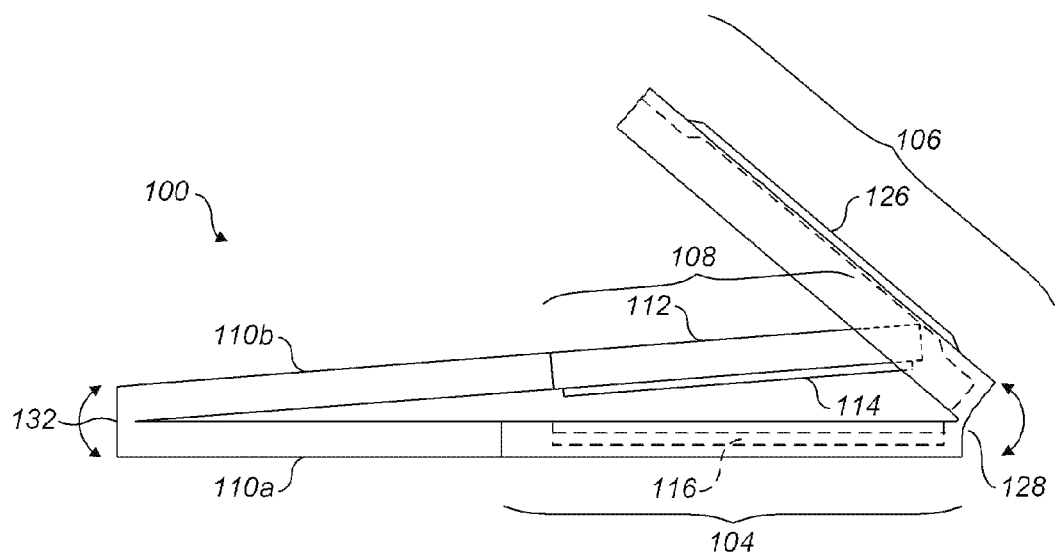

FIGS. 1a, 1b, and 1c show a biological sample collection device 100, according to a first embodiment of the invention. The device 100 comprises a body portion 102, which includes a storage medium holding portion (hereinafter "holding portion") 104 connected to a sample transfer means in the form of a cover 106, and a collection portion 108, which is connected to the body portion 102 by a movable arm 110. The holding portion 104 is arranged to hold a biological sample storage medium at a holding position, as is described below in relation to FIG. 1d. The device 100 can be arranged according to each of two configurations. In a first configuration, shown in FIG. 1a and hereinafter referred to as the "collection" configuration, the arm 110 is fully extended so that the collection portion 108 is in a "collection" position, spatially separated from the body portion 102, so as to be suitable for collection of a biological sample. In the collection configuration, the collection portion 108 is typically separated from the body portion 102 by a separation of between 5 and 15 cm. This degree of separation is sufficient to allow the collection portion 108 to be used to collect a sample, by, for example, inserting the collection portion 108 into the mouth of a human subject without access being obstructed by the body portion 102.

In a second configuration, shown in FIG. 1b, hereinafter referred to as the "transfer" configuration, the collection portion 108 is in a "transfer" position between the holding portion 104 and the cover 106, for transferring a collected biological sample from the sample collection surface to a sample storage medium held (not shown in FIGS. 1a to 1c) in the holding portion 104, as is described below in relation to FIGS. 2a and 2b.

In the present example, the collection portion 108 comprises a plate 112, and a sample collection medium 114 for collecting a biological sample. The collection medium 114 may comprise an absorbent material, such as a porous, hydrophilic, polyurethane foam pad. Typically, the collection medium 114 has a diameter of approximately 2.5 cm. The arm 110 comprises a proximal arm portion 110a and a distal arm portion 110b connected by a swivel joint, for example a hinge, hereinafter referred to as an arm hinge 132. The arm hinge 132 enables the collection portion 108 to be moved between the collection position and the transfer position. The arm hinge 132 allows the collection portion 108 to rotate about a fixed axis in a plane substantially perpendicular to the plane of the holding portion 104 (i.e. the plane that the holding portion 104 defines for holding a biological sample storage medium). The arm hinge 132 may be a film hinge formed by providing a section of the arm 110 that is thin relative to the rest of the arm 110, as shown in FIGS. 1a, 1b, and 1c. Alternatively, the arm hinge 132 may be a barrel hinge, as shown in FIG. 1e, with part of the arm hinge 132 on one part of the arm 110 and another part of the barrel hinge 132 on another part of the arm 110. The two parts of the arm hinge 132 are joined by a common axle 134. Other types of hinges may be used.

In some embodiments, the arm hinge 132 comprises a lock (not shown), which, when engaged, prevents movement of the arm 110. The lock may be a friction lock or may comprise interlocking features that provide resistance to movement of the arm 110, for example.

In the present example, the cover 106 is movably connected to the holding portion 104 by a hinge, hereinafter referred to as a cover hinge 128, which allows the cover to be moved from an open position, as shown in FIG. 1a, to a closed position, as shown in FIG. 1b.

Other types of movable connector may be used to connect the cover 106 to the holder portion 104; for example, in some embodiments, a sliding connection may be used, so that the cover can be slid between open and closed positions.

FIG. 1b shows locks 130, positioned either side of the arm 110, holding the cover 106 in a closed position. The locks 130 shown in FIG. 1b are a snap-shut latch type; however, other types of lock may be used. Further, in some embodiments, a single lock is used. The lock or locks 130 can be unlocked in order to allow the cover 106 to be reopened for removal of the biological sample storage medium for subsequent processing.

The cover 106 may further comprise a recess 126. The recess 126 is for locating the collection portion 108 in the transfer position. For that purpose it may have at least one dimension corresponding to a dimension of the collection portion 108. The recess 126 may also be used in transferring the sample from the collection medium 114 to the biological sample storage medium, as is described below in relation to FIGS. 2a and 2b.

Moving the device 100 between the transfer configuration and the collection configuration typically involves moving the cover 106 from the closed position to the open position (releasing any lock or locks as appropriate), and moving the arm 102 (again, releasing any lock or locks, where appropriate) from the transfer position with the collection medium 114 positioned facing the holding portion 104, to the collection position, with the arm fully extended. The reverse operation returns the device 100 to the transfer configuration. FIG. 1c shows the device 100 being moved between the transfer and collection configurations. The device 100 is typically stored in the transfer configuration prior to use, arranged in the collection configuration when collecting a sample, and then returned to the transfer configuration for transfer of the sample to the sample storage medium and subsequent storage and/or transportation.

Exemplary dimensions of the biological sample collection device are as follows. The body portion 102 is typically approximately 5.6 cm wide at its widest point. The length of the arm 110 from the body portion 102 to the collection portion 108 is typically approximately 13.5 cm. The length of the device 100 in the collection configuration, with the arm 110 fully extended and with the cover 106 in the closed position may be approximately 19 cm.

Figure 1D:
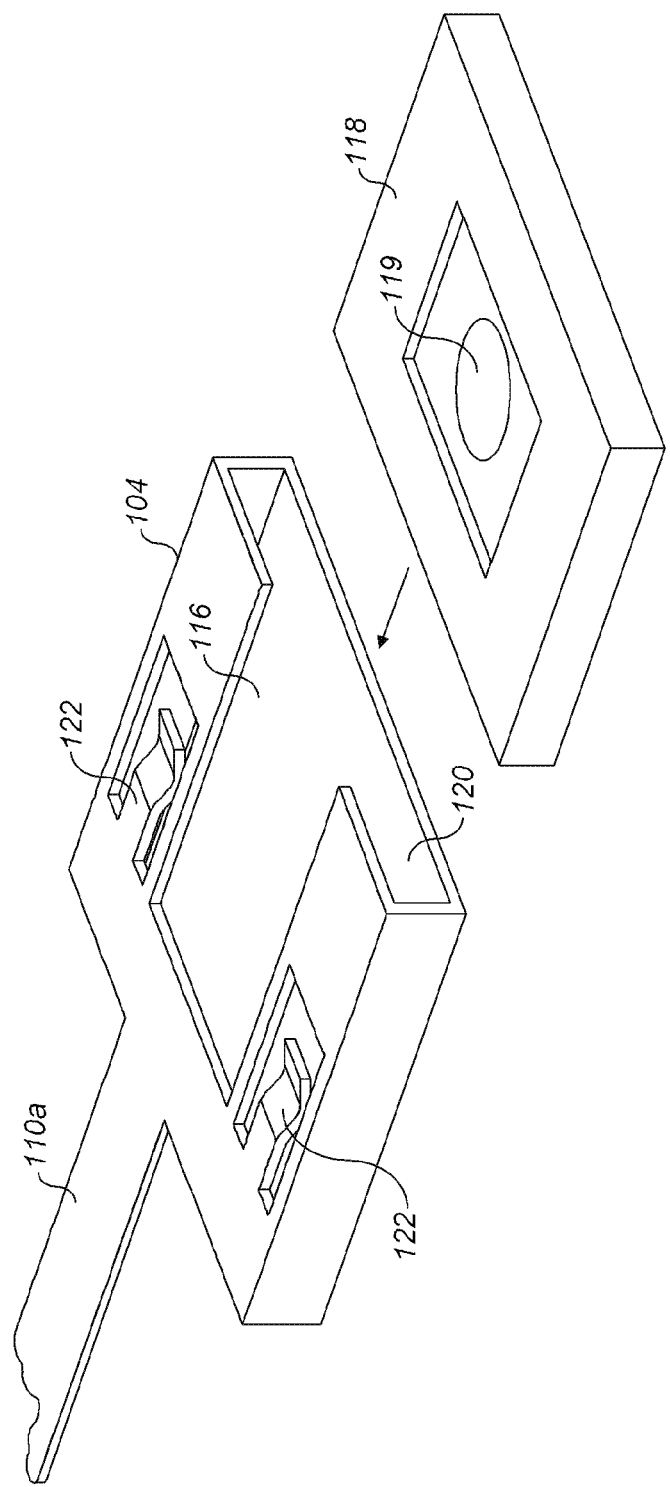
FIG. 1d shows a perspective view of a storage medium holding portion for use with a biological sample collection device according to an embodiment of the present invention.
Figure 1E:
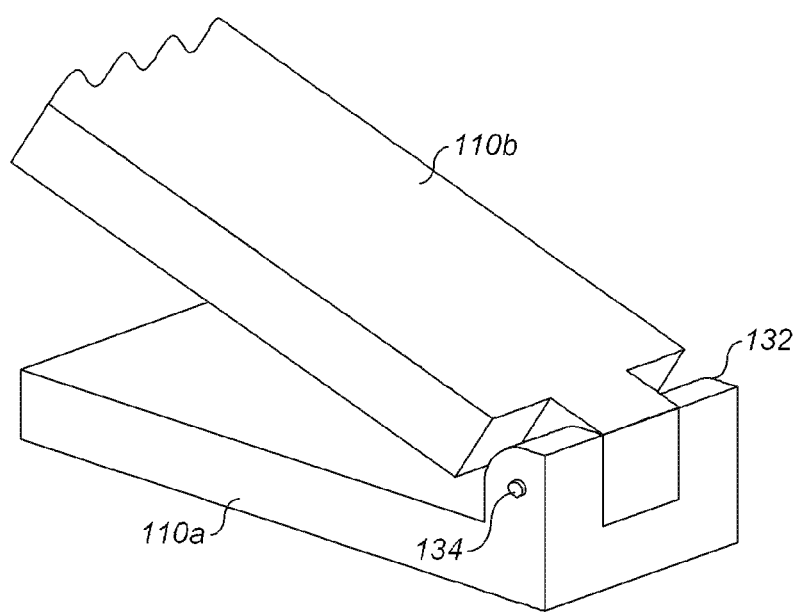
FIG. 1e shows a perspective view of a hinged portion for use with a biological sample collection device according to an embodiment of the present invention.

FIG. 1d shows an illustrative holding portion 104, comprising a compartment 116, for holding, at a holding position, a card 118 carrying a biological sample storage medium 119; for clarity, the collection portion 108 and the cover 106 are not shown in FIG. 1d. In the present example, the biological sample storage medium 119 is carried in a card 118; however, it will be understood that embodiments of the present invention are not limited to such examples, and other arrangements for carrying storage media 119 may be used.

The biological sample storage medium 119 is typically an absorbent membrane storage medium, and may be treated with chemicals to stabilise samples stored on the medium. Examples of suitable storage media 119 include untreated paper such as #903® brand paper (manufactured by Whatman, Inc.), and treated filter papers, such as FTA® and FTA® Elute brand paper (also manufactured by Whatman, Inc).

In the example of FIG. 1d, the holding portion 104 comprises an access slot 120 defining a holding position for holding the card 118, and facilitating the insertion and removal of the card 118 into and from the compartment 116. The internal dimensions of the compartment 116 may be arranged to correspond to the external dimensions of the card 118, so that the card 118 is held firmly in place by an interference fit. Alternatively or additionally, the compartment 116 may comprise other holding means for holding the card 118 in place; in the example shown in FIG. 1d, a sprung clamp 122 is provided to provide a clamping force to hold the card 118 in place. Other types of holding means may be used. In some embodiments, the compartment 116 comprises a door 124 (not shown) which may be opened to insert and remove the card 118, and closed to hold the card 118 in place.

In some embodiments, the card 118 comprises a removable protective film covering the biological sample storage medium 119. The removable protective film forms an impermeable seal that provides a barrier to prevent contamination of the storage medium 119. The removable protective film may be made from a flexible polymer or any other suitable material. Typically, the removable protective film is removed and discarded prior to use of the device. In some embodiments, the removable protective film may be replaceable, to provide protection to the storage medium 119 after use.

Use of the cover 106, and in particular the recess 126, to transfer a sample from the collection medium 114 to the storage medium 119 is now described in relation to FIGS. 2a and 2b. The collection portion 108 is shown in the transfer position and a card 118 holding a storage medium 119 is shown in place in the holding portion 104.

FIG. 2a shows the configuration of the cover 106 when no force is applied to the recess 126. The recess 126 is connected to the rest of the cover 106 by a flexible joint 202. The flexible joint 202 has sufficient resilience that when it is displaced by application of an external force, it will relax to that position when the force is removed. The collection portion 108 sits in the recess 126, and the collection medium 114 is separated from the storage medium 119.

When a force is applied to the top surface of the recess 126, the configuration of the cover 106 changes to that shown in FIG. 2b. The bottom face of the recess transmits the force to the plate 112 of the collection portion 108 and consequently, the collection portion 108 moves towards the holding portion, and the collection medium 114 is pushed against the storage medium 119 held on the card 118; if the collection medium 114 is loaded with a sample, at least some of the sample is thus transferred to the storage medium.

When the force is removed, the resilience of the flexible joint 202 provides a restoring force that causes the recess 126 to relax to the configuration shown in FIG. 2a. The arm 110 is also arranged to have sufficient resilience such that, after the force has been removed, it returns to the position shown in FIG. 2a, with the collection medium 114 of the collection portion 108 positioned apart from the storage medium 119 held on the card 118; the gap thus created facilitates drying of the sample after transfer to the storage medium.

Transfer of a biological sample from the collection medium 114 to the biological sample storage medium 119 may thus be implemented without the operator coming into direct contact with the sample collection portion 108. Furthermore, since the transfer of the sample is implemented by the use of a sample transfer means such as a cover 106, with the collection portion 108 being located between the cover 106 the holding portion 104, the sample transfer means can also be used to hold the collection portion in place subsequent to transfer of the sample. This is advantageous since, in order to improve traceability of the sample, after transfer of the sample to the biological sample storage medium, the latter is typically not removed from the device 100, with the device 100 including the storage medium 119 storing the sample instead being placed into a bag and transported to a laboratory or other facility for processing; it is therefore advantageous to hold the collection portion 108 in place in the transfer position, in order that any portion of the sample remaining on the collection medium 114 does not spread within the bag. The cover 106, or other sample transfer means, can thus be used to perform a dual function, simplifying the structure of the device 100. Further, the cover 106 may be arranged to be substantially flat, so that no protrusions are present in the device 100, preventing the bag in which it is contained from being punctured or otherwise damaged during transport.

Figure 3A:
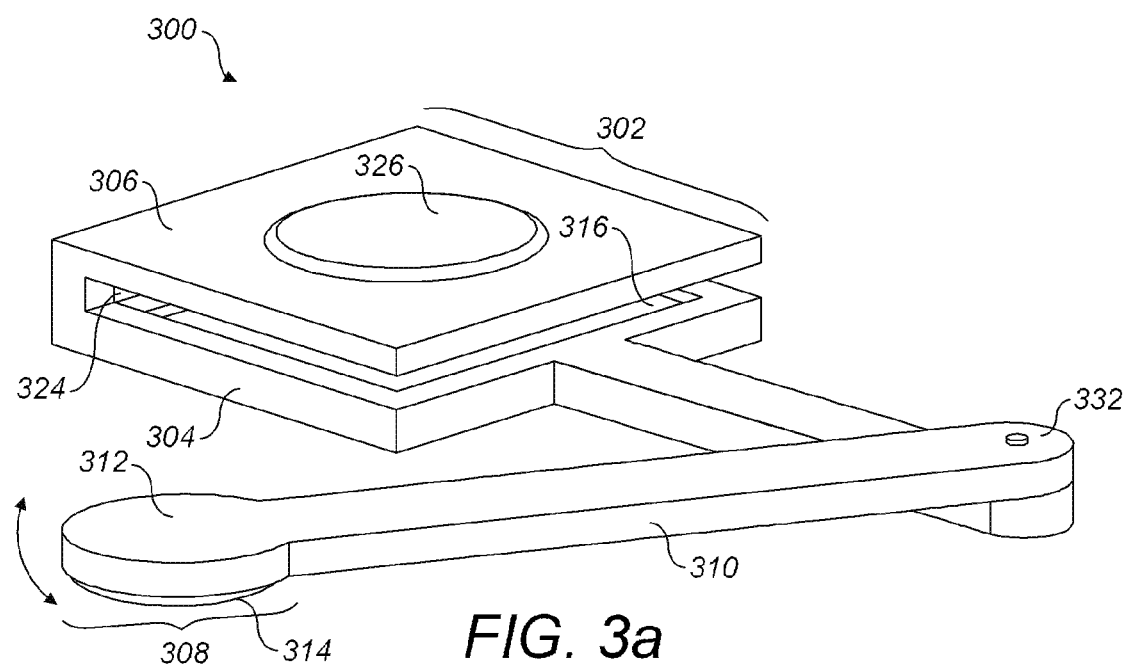
FIG. 3a shows a first perspective view of a biological sample collection device according to a second embodiment of the present invention.
Figure 3B:
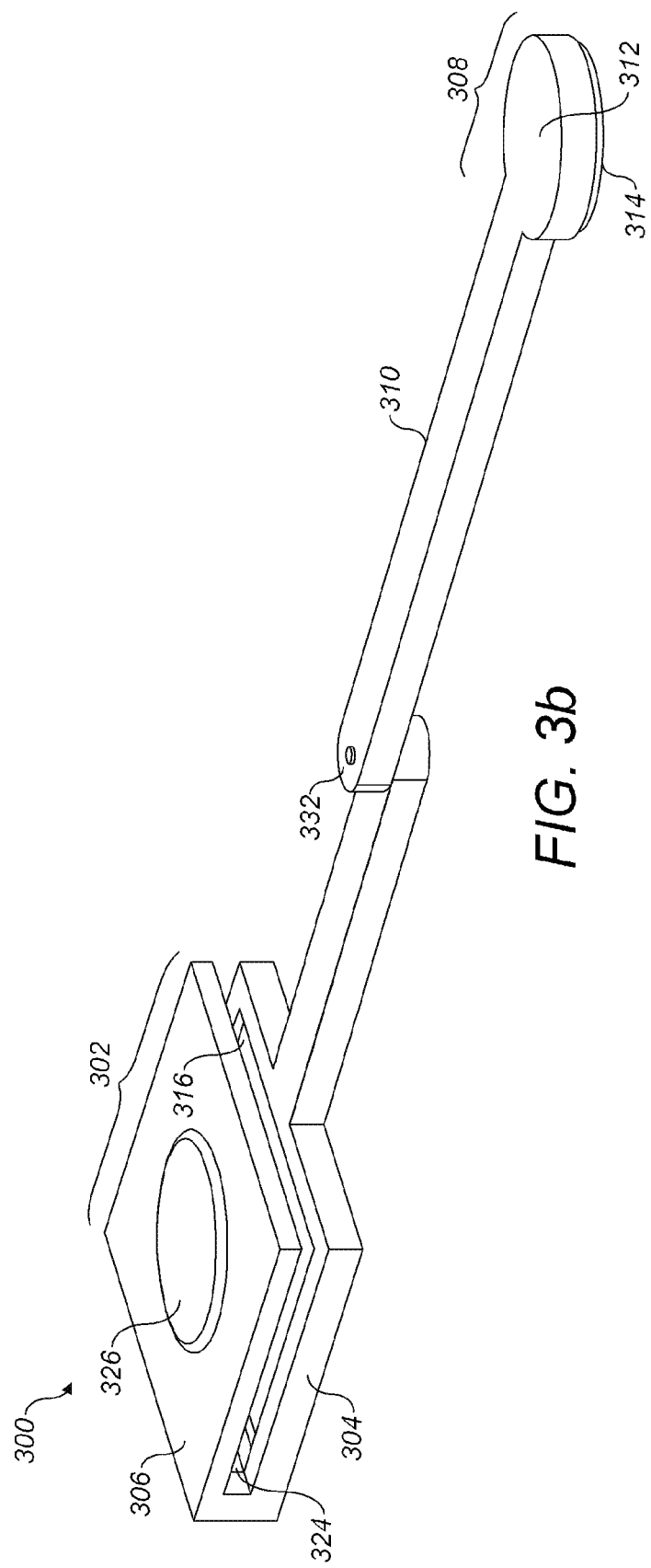
FIG. 3b shows a second perspective view of a biological sample collection device according to the second embodiment of the present invention.

FIGS. 3a and 3b shows a biological sample collection device 300 in accordance with a second embodiment of the present invention. The biological sample collection device 300 of this embodiment comprises a body portion 302, which includes a holding portion 304 connected to a cover 306, and a collection portion 308, which is connected to the body portion 302 by a movable arm 310. The collection portion 308 comprises a plate 312 and a collection medium 314. The holding portion 304 comprises a compartment 316 for holding a biological sample storage medium (not shown). Unless otherwise indicated, the various components of the biological sample collection device 300 of this second embodiment have the same features of the corresponding components of the biological sample collection device 100 of the first embodiment described above.

In the embodiment of FIG. 3a, the arm 310 is able to rotate about a swivel joint 332, which allows the collection portion 308 to rotate about a fixed axis in a plane substantially parallel to the plane of the holding portion 304 (i.e. the plane that the holding portion 304 defines for holding a biological sample storage medium). A gap is provided between the holding portion 304 and the cover 306, through which the collection portion 308 may pass; the gap is preferably large enough so that the collection portion can pass through easily without any biological sample on the collection medium 314 coming into contact with any part of the body portion 302. The flexibility of the arm 310 allows the collection portion 308 to be manoeuvred into the gap between the holding portion 304 and the cover 306, and subsequently enables the collection portion to locate in the recess 320. Accordingly, in this embodiment, the cover 306 may be fixedly connected to the holding portion 304, with no cover hinge or other movable connection used.

Thus, the collection portion 308 may be moved between a collection position, in which the arm 310 is fully extended as shown in FIG. 3b, and a transfer position (not shown in the Figures) in which the collection portion 308 is located between the cover 306 and the holding portion 304.

When the collection portion 308 is in the collection position (i.e. the device 300 is in the collection configuration), the biological sample collection device 300 is in a collection configuration, suitable for collecting a biological sample, as described above in relation to FIG. 1a.

When the collection portion 308 is in the transfer position (i.e. the device is in the transfer configuration), the collection medium 312 is held apart from the holding portion 304, so that it is not held in contact with a biological storage medium held therein. A biological sample held on the biological sample collection medium may be transferred to the sample storage medium by use of a recess 326, as described above in relation to FIGS. 2a and 2b.

Alternative Arrangements

Figure 4A:
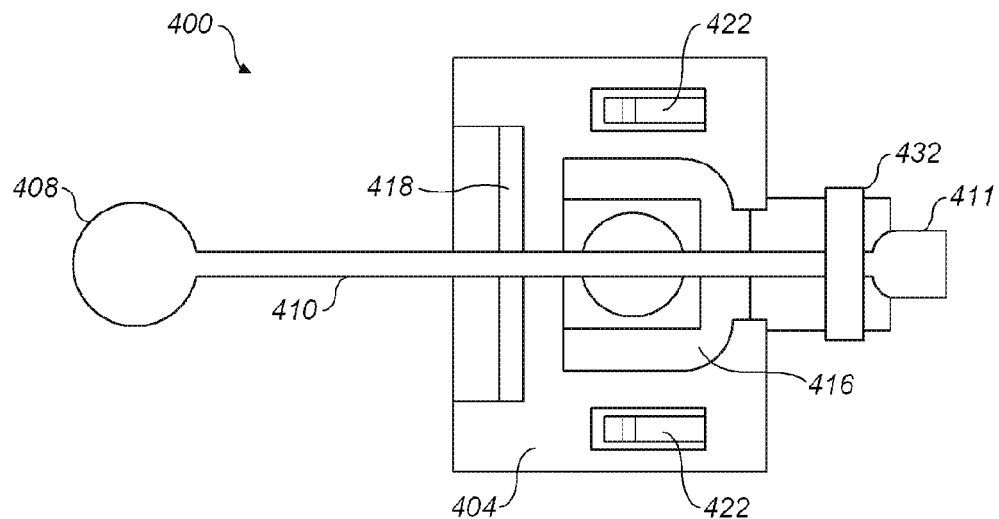
FIG. 4a shows a plan view of an alternative arrangement of a biological sample collection device in a first configuration.
Figure 4B:
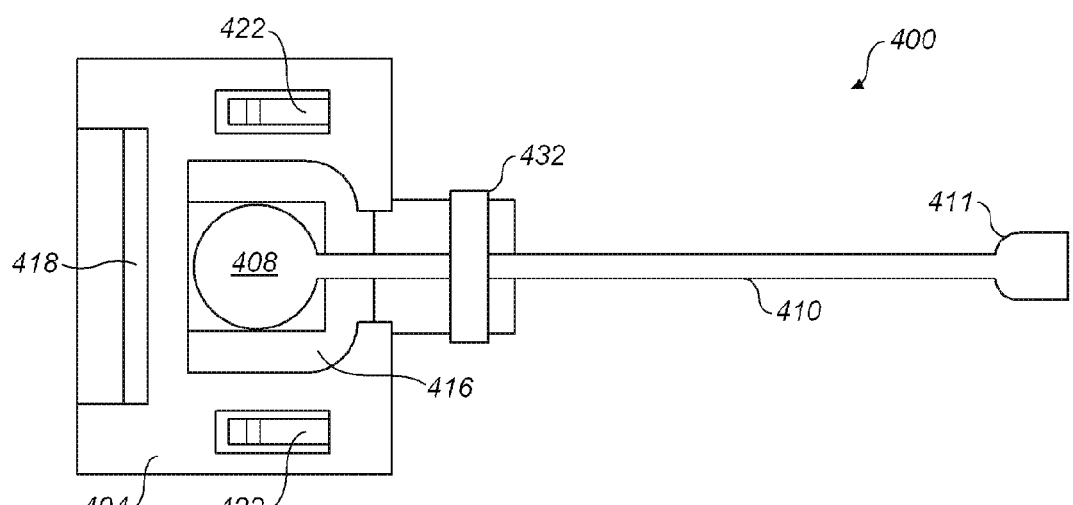
FIG. 4b shows a plan view of the biological sample collection device of FIG. 4a in a second configuration.

FIGS. 4a and 4b show a first alternative arrangement for a biological sample collection device 400 comprising a collection portion 408 and a holding portion 404, the collection portion 408 being connected to the holding portion 404 by an arm 410. Unless otherwise indicated, the various components of this first alternative biological sample collection device 400 have the same features as the corresponding components of the biological sample collection device 100 of first embodiment described above.

The holding portion 404 comprises a compartment 416 for holding a card 418 or other biological sample holding medium; the arrangement shown in FIGS. 4a and 4b includes sprung clamps 422 for holding a biological sample storage medium, which may be held on a card 114 as described above, in place in the holding portion 404. The collection portion 408 is movably connected to the holding portion 404 by a slide joint 432 which allows the arm 410 to be extended and retracted, so that the collection portion 408 can move between a collection position, in which the arm 410 is fully extended as shown in FIG. 4a and a transfer position, in which the collection portion 408 is located so that the collection medium is arranged facing the sample storing portion, as shown in FIG. 4b. A handle 411 is provided on the arm 412 at an end opposite to that at which the collection portion 408 is located to facilitate extension and retraction of the arm 410. When the sample collection portion 408 is in the transfer position, the operator may press directly on the sample collection portion 408 in order to transfer a sample collected on the sample collection medium to the biological sample storage medium. Although not shown, a tab lock may be incorporated into the arrangement to maintain the collection portion 408 in a position separated from the card 418 or other biological sample storage medium for subsequent storage and shipping.

This first alternative arrangement of a biological sample collection device 400 is compact, and requires no parts protruding out of the plane of the device, making it convenient for storage and transportation.

Figure 5:
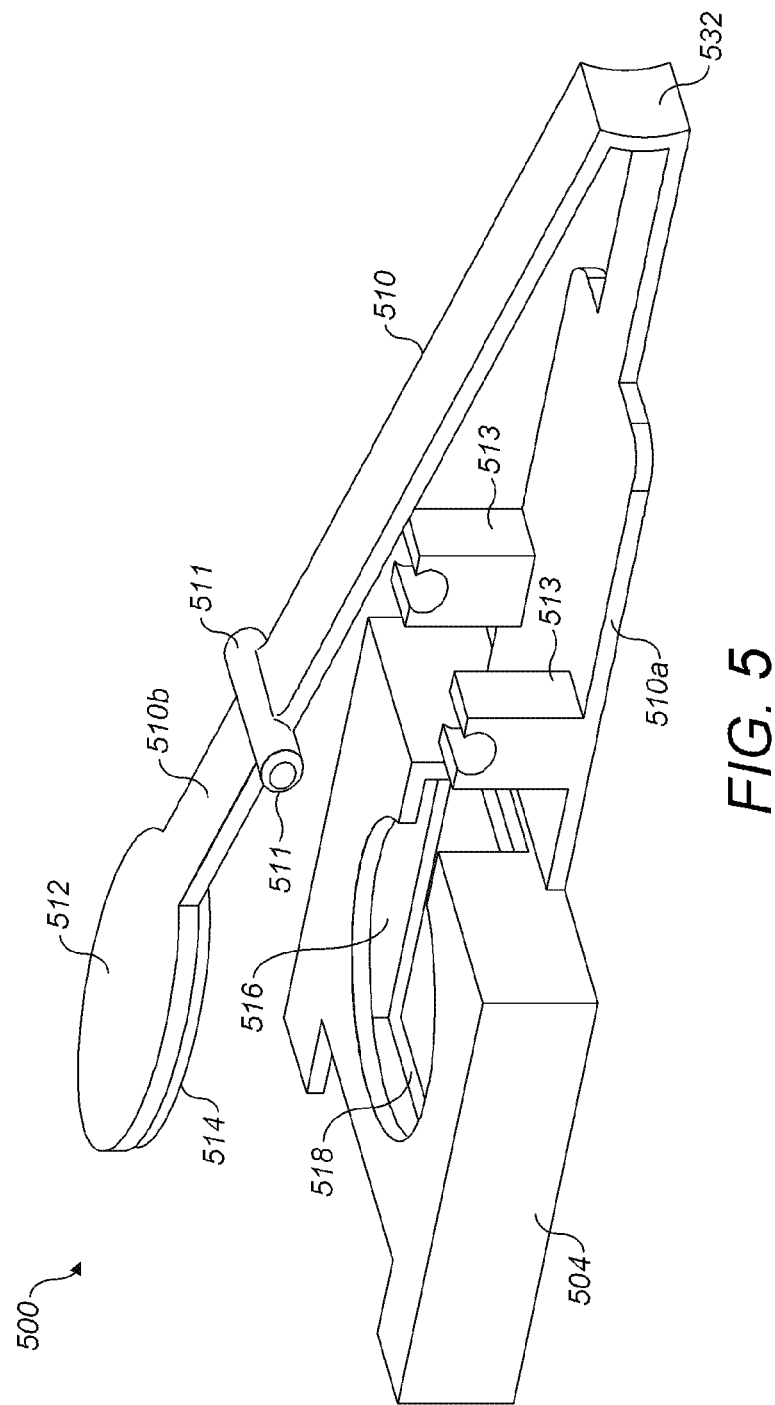
FIG. 5 shows a perspective view of another alternative arrangement of a biological sample collection device.

FIG. 5 shows a second alternative arrangement for a biological sample collection device 500 comprising a collection portion 512 and a holding portion 504. Unless otherwise indicated, the various components of this second alternative biological sample collection device 500 may have the same features as the corresponding components of the biological sample collection device 100 of first embodiment described above. In particular, the collection portion 512 is connected to the holding portion 504 by a movable arm 510, which includes a hinge 532 or other swivel joint, allowing the collection portion 512 to move between a transfer position and a collection position in the same way as the collection portion 108 described above in relation to FIGS. 1a, 1b, and 1c.

The device 500 comprises a lock for locking the collection portion in the transfer position. In the example of FIG. 5, the lock comprises a stub 511 located on an each outer edge of a distal portion 510b of the arm 510, each of the stubs corresponding in size and position to a socket 513 located on the outer edges of a proximal portion 510a of the arm. In the example shown there are two sockets 513 arranged to receive respective stubs 511. The stubs 511 engage with the sockets 513 when the stubs 511 are brought into physical contact with the sockets 513 and an appropriately directed force is applied. The configuration of the sockets 513 is such that the stubs 511 may be removed from the sockets 513 by the application of an appropriate force applied in the opposite direction to the force that is required to engage the locks. When transferring a sample from the sample collection medium to a biological sample storage medium, an operator may apply a force directly to the sample collection portion 502, pushing the sample collection medium 514 against the card 518 or other biological sample storage medium held in the compartment 516 of the holding portion 408. Since there is a lock located on each side of the arm, the sample collection portion 512 can be held firmly in position during transfer of the sample, enabling an even transfer onto the sample storage medium.

Although the arrangements described above in relation to FIG. 4 and FIG. 5 do not include any cover or other sample transfer means, it will be understood that these arrangements could be modified to include such sample transfer means, in accordance with embodiments of the present invention.

Typically, the biological sample collection devices 100, 300, 400, 500 described above are supplied with a card 118 in place in the holding portion 104. However, in some circumstances the card 118 may be supplied separately from the device 100. Typically, the device 100, 300, 400, 500 is for single-use; however, in some applications the card 118 and/or the collection medium 110 may be removed and replaced.

The biological sample devices 100, 300, 400, 500 described above may comprise an identification tag comprising identification information. The tag may be printed directly onto the device 100, or be incorporated onto an adhesive label, or be added to the device 100 by any other means. The tag may comprise textual and/or graphical information including sample identification numbers, donor details, and/or a barcode relating to such details stored remotely in a database. Other types of tag may be used, for example an RFID tag.

The device 100, 300, 400, 500 may be manufactured from a plastics material using an injection moulding process. The plastics material should be compliant enough to allow temporary deformation of resilient parts of the device 100, 300, 400, 500 that are required to deform, when subjected to a suitable externally applied force, and to relax to their original positions, upon removal of the externally applied force. The plastics material may also be selected such that it does not easily build up a static charge when handled, since such static charge can cause problems such as different collection devices 100, 300, 400, 500 sticking together, interfering with handling. An exemplary suitable plastics material is polypropylene homopolymer resin. However, any other suitable plastics material could be used as an alternative.

The above described biological sample collection devices 100, 300, 400, 500 are typically used for collection of biological samples such as saliva, blood or other bodily fluids. Samples collected by operation of the device 100, 300, 400, 500 may be subjected to processing such as DNA or RNA amplification procedures, for example as polymerase chain reaction (PCR) procedures.

The above embodiments are to be understood as illustrative examples of the invention. Further embodiments of the invention are envisaged. For example, in some cases it may be desirable to remove and discard the collection portion after use, effectively converting the body portion 102 into a stand-alone storage device. For this purpose, a weak point may be included in the arm, or where the arm connects to the body portion 102.

Although the use of a recess portion 126, 326 is described above in relations to the first and second embodiments for the transfer of the biological sample, in some embodiments, no recess is used. Instead the cover 106, 306 may be arranged to be sufficiently flexible such that a pushing force exerted thereon forces the collection medium 114, 312 to press against the biological sample storage medium, for example.

In addition, although the swivel joints 132, 332, 532 described above allowed swivelling in one plane only, embodiments of the invention are not limited to such movement; for example, in some embodiments a ball and socket joint may be used, which enables swivelling in any arbitrary plane.

Further, it is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A biological sample collection device, comprising:
a collection portion carrying a biological sample collection medium; and
a body portion comprising a storage medium holding portion for holding a biological sample storage medium at a holding position, and a sample transfer cover portion,
the collection portion being movably connected to the body portion, whereby the biological sample collection device is capable of being configured according to a first configuration and according to a second, different, configuration, wherein:
in said first configuration, the collection portion is at a first position spatially separated from the body portion for collecting a biological sample on the biological sample collection medium; and
in said second configuration, the collection portion is at a second position at least partly between the sample storage medium holding portion and the sample transfer cover portion, and the sample transfer cover portion is operable to apply a force to the collection portion, whereby said collection portion is compelled towards said holding position so that, when the storage medium holding portion holds a biological sample storage medium, the biological sample collection medium is pushed against said biological sample storage medium;
wherein when the collection portion is at said second position, the collection portion is at least partly enclosed by the sample transfer cover portion and the storage medium holding portion; and
wherein said sample transfer cover portion is movably connected to said storage medium portion for movement between an open position, for facilitating movement of the collection portion from said first position to said second position, and a closed position for enabling operation of the sample transfer cover portion to apply said force.

2. The biological sample collection device of claim 1, wherein, when the collection portion is at said second position, the biological sample collection medium is in a position separated from said holding position.

3. The biological sample collection device of claim 2, wherein the collection portion is connected to the body portion via an arm portion which is arranged to flex from said second position towards the holding position in response to said force.

4. The biological sample collection device of claim 1, wherein the sample transfer cover portion includes a compressible recess portion, and said operation of the sample transfer cover portion comprises compression of the recess portion.

5. The biological sample collection device of claim 4, wherein said recess portion has at least one dimension substantially matching a corresponding dimension of the collection portion, so that the collection portion may locate in said recess portion when the device is in the second configuration.

6. The biological sample collection device of claim 1, wherein the collection portion is connected to the storage medium holding portion via a swivel joint, which enables the collection portion to move between said first position and said second position.

7. The biological sample collection device of claim 6, wherein the storage medium holding portion defines a plane for holding said biological sample storage medium, and the swivel joint enables the collection portion to swivel about an axis substantially within said plane.

8. The biological sample collection device of claim 6, wherein the storage medium holding portion defines a plane for holding said biological sample storage medium, and the swivel joint enables the collection portion to swivel about an axis substantially perpendicular to said plane.

9. The biological sample collection device of claim 8, wherein a gap is provided between said sample transfer cover portion and said storage medium holding portion and the swivel joint enables the collection portion to move through said gap.

10. The biological sample collection device of claim 1, wherein the collection portion is connected to the storage medium holding portion via a slide joint, which enables sliding movement of the collection portion between said first position and said second position.

11. The biological sample collection device of claim 1, comprising a lock for locking said sample transfer cover portion in at least one of said closed position and said open position.

12. The biological sample collection device of claim 1, comprising a lock for locking said collection portion in at least one of said first position and said second position.

13. The biological sample collection device of claim 1, wherein the sample collection medium comprises an absorbent material for absorbing a liquid biological sample.

14. The biological sample collection device of claim 1, comprising a biological sample storage medium held in said storage medium holding portion.

15. The biological sample collection device of claim 14, wherein the biological sample storage medium is removable from said storage medium holding portion.

16. The biological sample collection device of claim 1, wherein the biological sample storage medium comprises a planar membrane for absorbing liquid biological samples.

17. The biological sample collection device of claim 16, wherein the biological sample storage medium is held on a card.

18. The biological sample collection device of claim 1, made from a plastics material.

* * * * *